(12) United States Patent
Ah et al.

(10) Patent No.: US 8,969,099 B2
(45) Date of Patent: Mar. 3, 2015

(54) MICROANALYSIS METHODS AND SYSTEMS USING FIELD EFFECT TRANSISTOR

(75) Inventors: Chil Seong Ah, Daejeon (KR); Jong-Heon Yang, Daejeon (KR); Chan Woo Park, Daejeon (KR); Chang-Geun Ahn, Daejeon (KR); Gun Yong Sung, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 465 days.

(21) Appl. No.: 13/233,684

(22) Filed: Sep. 15, 2011

(65) Prior Publication Data

US 2012/0070910 A1    Mar. 22, 2012

(30) Foreign Application Priority Data

Sep. 16, 2010 (KR) .................... 10-2010-0091207
Jan. 28, 2011 (KR) .................... 10-2011-0008837

(51) Int. Cl.
| | | |
|---|---|---|
| G01N 27/00 | (2006.01) | |
| G01N 27/414 | (2006.01) | |
| G01N 27/327 | (2006.01) | |
| G01N 33/543 | (2006.01) | |
| G01N 33/53 | (2006.01) | |
| G01N 33/58 | (2006.01) | |
| G01N 33/553 | (2006.01) | |
| G01N 21/65 | (2006.01) | |

(52) U.S. Cl.
CPC ........ G01N 27/4146 (2013.01); G01N 27/4145 (2013.01); G01N 27/414 (2013.01); G01N 27/3278 (2013.01); G01N 33/54373 (2013.01); G01N 33/53 (2013.01); G01N 33/54346 (2013.01); G01N 33/587 (2013.01); G01N 33/553 (2013.01); G01N 33/585 (2013.01); G01N 21/658 (2013.01)
USPC ..................... 436/501; 435/287.2; 435/287.1; 435/287.9; 435/288.7; 435/7.1; 435/7.92; 435/7.94; 436/525; 422/69; 422/82.01; 422/68.1

(58) Field of Classification Search
None
See application file for complete search history.

(56) References Cited

U.S. PATENT DOCUMENTS 5,466,348 A * 11/1995 Holm-Kennedy ............ 205/775

FOREIGN PATENT DOCUMENTS

KR    1020060038676 B1    4/2006

OTHER PUBLICATIONS

Park et al., Array-Based Electrical Detection of DNA with Nanoparticle Probes, 2002, vol. 295, pp. 1503-1506.*

(Continued)

Primary Examiner — Melanie Y Brown
Assistant Examiner — Erik B Crawford

(57) ABSTRACT

Provided is a microanalysis method and system using a Field Effect Transistor (FET). The microanalysis method includes a channel region having a receptor molecule fixed; forming a nano-particle conjugate in the channel region by supplying a sample for test and the nano-particle conjugate to the FET; growing a probe material on the channel region; and measuring a current flowing through the channel region, wherein the receptor molecule is a material that is selectively bonded to a target molecule in the sample for test.

7 Claims, 14 Drawing Sheets

(56) References Cited

OTHER PUBLICATIONS

Liu et al., Exploiting Sub-threshold and Above-threshold Characteristics in a Silver-Enhanced Gold Nanoparticle Based Biochip, Sep. 2009, 31st Annual International Conference of the IEEE EMBS, pp. 3810-3813.*

Ja-An Annie Ho et al., "Diagnostic Detection of Human Lung Cancer-Associated Antigen Using a Gold Nanoparticle-Based Electrochemical Immunosensor", Analytical Chemistry, Jul. 15, 2010, pp. 5944-5950, vol. 82, No. 14, American Chemical Society.

* cited by examiner

MICROANALYSIS METHODS AND SYSTEMS USING FIELD EFFECT TRANSISTOR

CROSS-REFERENCE TO RELATED APPLICATIONS

This U.S. non-provisional patent application claims priority under 35 U.S.C. §119 of Korean Patent Application Nos. 10-2010-0091207, filed on Sep. 16, 2010, and 10-2011-0008837, filed on Jan. 28, 2011, the entire contents of which are hereby incorporated by reference.

BACKGROUND OF THE INVENTION

The present invention disclosed herein relates to a microanalysis, and more particularly, to microanalysis methods and systems using a Field Effect Transistor (FET).

A technique for detecting certain bio-molecules by using the FET has been suggested. The FET for a biosensor includes source/drain electrodes and a channel pattern therebetween. Receptor molecules for a specific bonding with target bio-molecules are fixed at the channel pattern.

If the target bio-molecules are included in a sample, they are specifically bonded with the receptor molecules, thereby changing an electrical state of the channel pattern. For example, the channel pattern may be in an accumulation, depletion, or reverse state according to an amount of the specifically bonded target bio-molecules. Accordingly, whether there are the target bio-molecules may be determined by measuring a current flowing through the channel pattern.

Meanwhile, according to typical suggested FET bio-sensing techniques, an electrical state change of the channel pattern or a magnitude of the channel current, which is caused due to a specific bonding, is small. Accordingly, reproducibility is not obtained from measurement results. Although some new techniques have been suggested to obtain reproducibility from measurement results, these raise other technical limitations such as complexity in a measurement process or a sensor structure.

SUMMARY OF THE INVENTION

The present invention provides a microanalysis method for amplifying channel current.

The present invention also provides a microanalysis method for quantitative detection of bio-molecules.

The present invention also provides a microanalysis method for obtaining simplicity during a measurement process.

The present invention also provides a microanalysis system for quantitative detection of bio-molecules.

Embodiments of the present invention provide microanalysis methods including: preparing a Field Effect Transistor (FET) including a channel region having a receptor molecule fixed; forming a nano-particle conjugate in the channel region by supplying a sample for test and the nano-particle conjugate to the FET; growing a probe material on the channel region; and measuring a current flowing through the channel region, wherein the receptor molecule is a material that is selectively bonded to a target molecule in the sample for test.

In some embodiments, the nano-particle conjugate may be selectively bonded to the target molecule; and the probe material may be a charged material that is selectively bonded to the nano-particle conjugate.

In other embodiments, the forming of the nano-particle conjugate in the channel region may include using an immune reaction between the target molecule and the receptor molecule.

In still other embodiments, the growing of the probe material may be performed using a plating operation.

In even other embodiments, the forming of the nano-particle conjugate and the growing of the probe material may be performed under a wet environment.

In yet other embodiments, the measuring of the current may be performed under a dry environment after the growing of the probe material.

In further embodiments, the measuring of the current may include: a first current measuring operation performed before the growing of the probe material; and a second current measuring operation performed after the growing of the probe material, wherein the first current measuring operation is performed under a wet or dry environment; and wherein the second current measuring operation is performed under a wet or dry environment.

In still further embodiments, the target material may be a bio-molecule; and the nano-particle conjugate and the probe material may include a metallic element.

In other embodiments of the present invention, microanalysis systems include: at least one FET having a channel region with a receptor molecule fixed; a first supplying unit supplying a sample for test and a nano-particle conjugate; a second supplying unit supplying a probe material; a measuring unit measuring a current flowing through the channel region; a first reaction controlling unit controlling a process for forming the nano-particle conjugate in the channel region; and a second reaction controlling unit controlling a process for growing the probe material in the channel region.

In some embodiments, the FET may use silicon as the channel region.

In other embodiments, the FET may use a carbon nanotube as the channel region.

In still other embodiments, the FET, the measuring unit, the first and second supplying units, and the first and second reaction controlling units may constitute one of first and second modules separated, the first module including the FET, the second module including the second supplying unit.

In even other embodiments, the receptor material may be a material that is selectively bonded to a target molecule in the sample for test; the nano-particle conjugate is a material that may be selectively bonded to the target molecule; and the probe material may be a material that is selectively bonded to the nano-particle conjugate.

In yet other embodiments, the microanalysis systems may further include a main controlling unit controlling operations of the first and second supplying units, the first and second reaction controlling units, and the measuring units.

In further embodiments, the at least one FET may include a plurality of separately operating transistors, each of the transistors including a source electrode, a drain electrode and a silicon pattern therebetween.

BRIEF DESCRIPTION OF THE DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings.

DETAILED DESCRIPTION OF PREFERRED EMBODIMENTS

Figure 1:
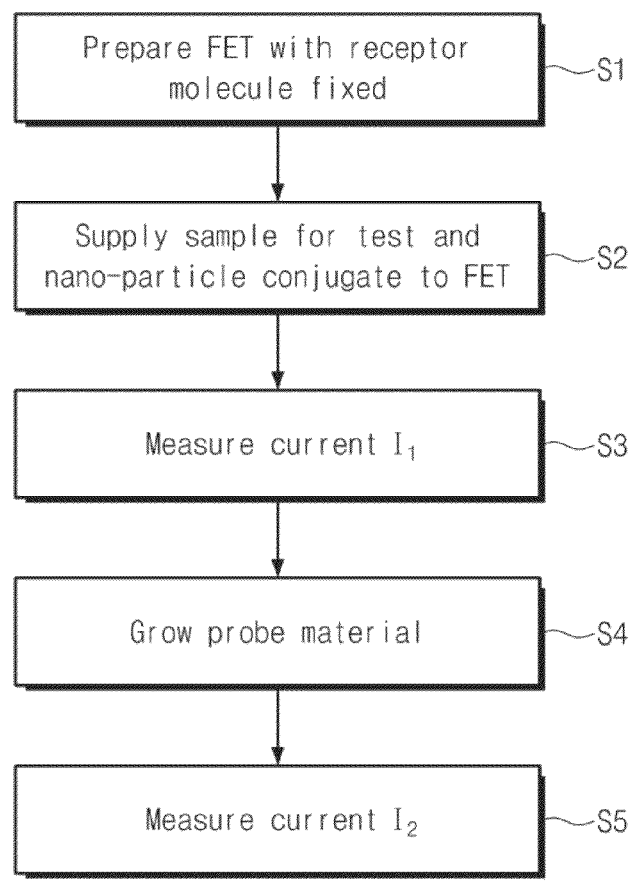
FIG. 1 is a flowchart illustrating a microanalysis method according to some embodiments of the present invention.

Preferred embodiments of the present invention will be described below in more detail with reference to the accompanying drawings. The present invention may, however, be embodied in different forms and should not be constructed as limited to the embodiments set forth herein. Rather, these embodiments are provided so that this disclosure will be thorough and complete, and will fully convey the scope of the present invention to those skilled in the art.

These terms are only used to distinguish one element from another element. It will also be understood that when a layer (or film) is referred to as being 'on' another layer or substrate, it can be directly on the other layer or substrate, or intervening layers may also be present. In the figures, the dimensions of layers and regions are exaggerated for clarity of illustration. In the drawings, the dimensions of layers and regions are exaggerated for clarity of illustration. It will be understood that although the terms first and second are used herein to describe various elements, these elements should not be limited by these terms. Hereinafter, it will be described about an exemplary embodiment of the present invention in conjunction with the accompanying drawings. These terms are used only to discriminate one region or layer from another region or layer. Therefore, a layer referred to as a first layer in one embodiment can be referred to as a second layer in another embodiment. An embodiment described and exemplified herein includes a complementary embodiment thereof.

FIG. 1 is a flowchart illustrating a microanalysis method according to some embodiments of the present invention. FIGS. 2 through 6 are perspective views illustrating a microanalysis method according to some embodiments of the present invention.

Figure 2:
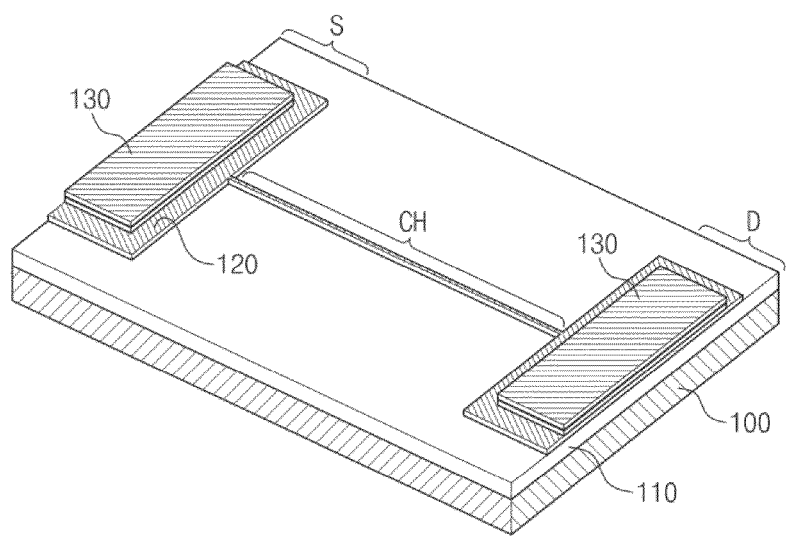
FIGS. 2 through 6 are perspective views illustrating a microanalysis method according to some embodiments of the present invention.
Figure 3:
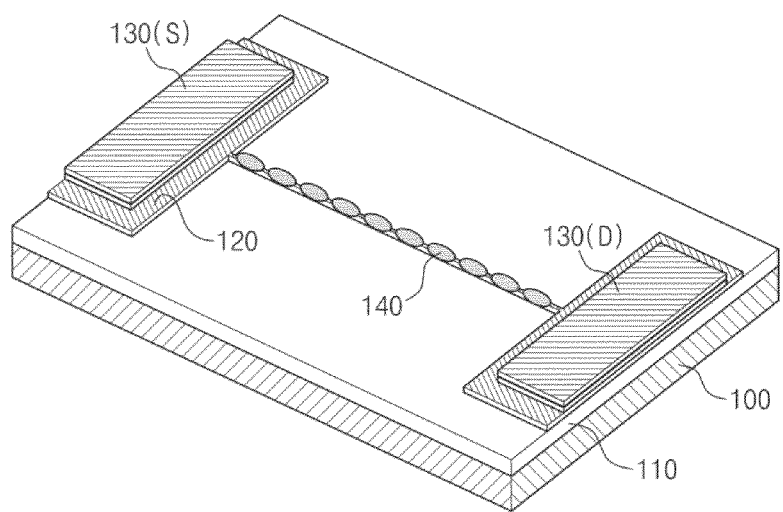

Referring to FIG. 1, as shown in FIGS. 2 and 3, after a Field Effect Transistor (FET) having a channel region CH is prepared, receptor molecules 140 are fixed on the channel region CH in operation 51.

Figure 7A:
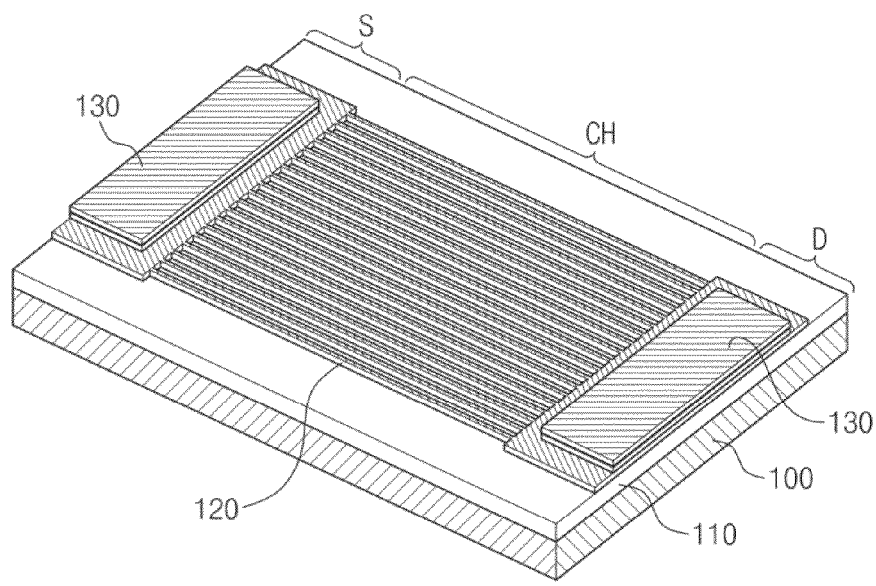
FIGS. 7A and 7B are perspective views illustrating a FET according to another embodiment of the present invention.
Figure 7B:
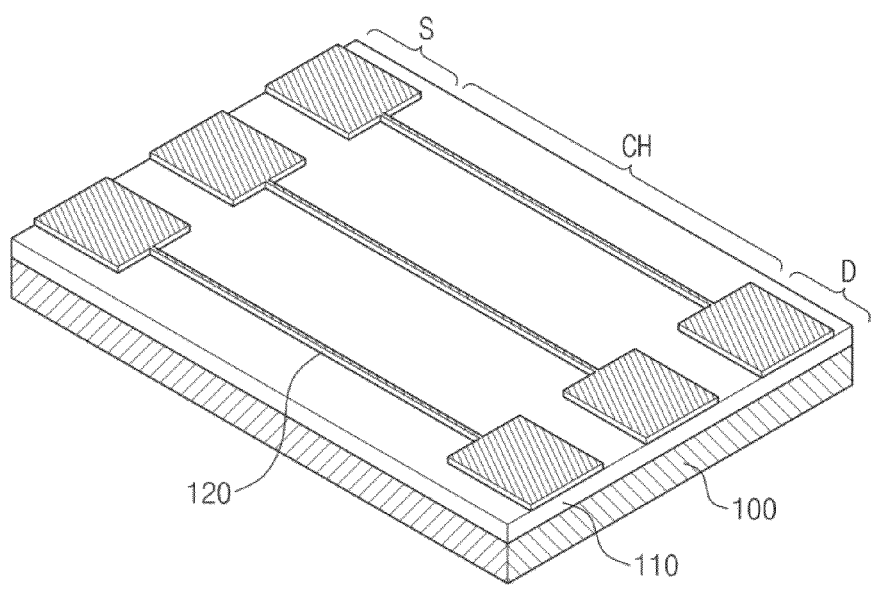

According to the some embodiments of the present invention, as shown in FIG. 2, the FET may be realized using a Silicon-On-Insulator (SOI) substrate including a lower substrate 100, an insulation layer 110, and a silicon layer 120. The silicon layer 120 may be patterned to constitute source and drain electrodes S and D and the channel region CH disposed therebetween. The channel region CH may have a p or n type conductor. Metallic pads 130 may be formed as a structure for electrical connection with an external electronic device on the source and drain electrodes S and D. Moreover, according to other embodiments of the present invention, the channel region CH of the FET, as shown in FIGS. 7A and 7B, may include a plurality of silicon patterns connecting between the source and drain electrodes S and D. As shown in FIG. 7A, the plurality of silicon patterns used as the channel region CH may be commonly connected to one source electrode S and one drain electrode D. Or, as shown in FIG. 7B, the source and drain electrodes S and D may be spatially separated to be independently driven and the plurality of silicon patterns may be connected to the respectively different source and drain electrodes S and D. Additionally, the silicon patterns used as the channel region may be configured to have the same dimension and during a measurement process, the channels having the same dimension are simultaneously measured to obtain a signal.

The receptor molecules 140 may be a material that is selectively bonded to the target material. For example, if the target material is a bio-molecule, the receptor molecules 140 may be a material that may be specifically bonded to the target material through an immune reaction. However, the receptor molecules 140 may vary according to the kinds of materials (hereinafter, referred to as a target material or a target molecule) to be detected but the technical scopes of the present invention are not limited to the receptor molecules 140 or the kinds of the target material.

Figure 4:
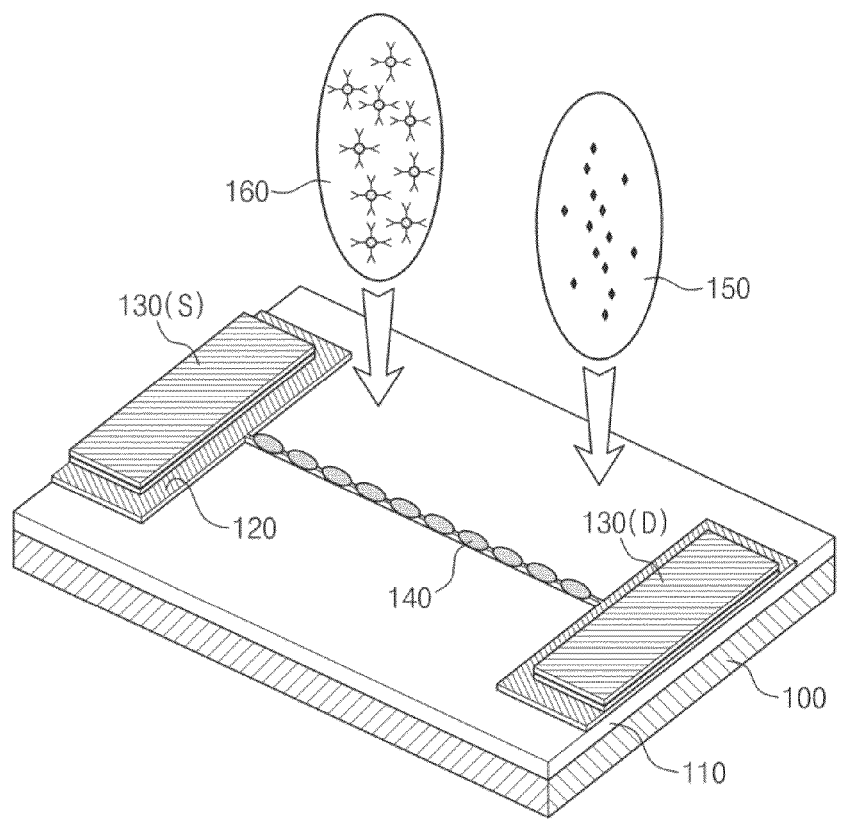

Referring to FIG. 1 again, as shown in FIG. 4, a sample for test including target molecules 150 and a solution including nano-particle conjugates 160 are supplied to the channel region CH of the FET in operation S2.

The receptor molecules 140 may be a material that may be specifically bonded (i.e., selectively bonded) to the target molecules 150, as mentioned above. In this case, if the sample for test includes the target molecules 150, the target molecules 150 may be formed on the surface of the channel region CH through the receptor molecules 140.

Figure 5:
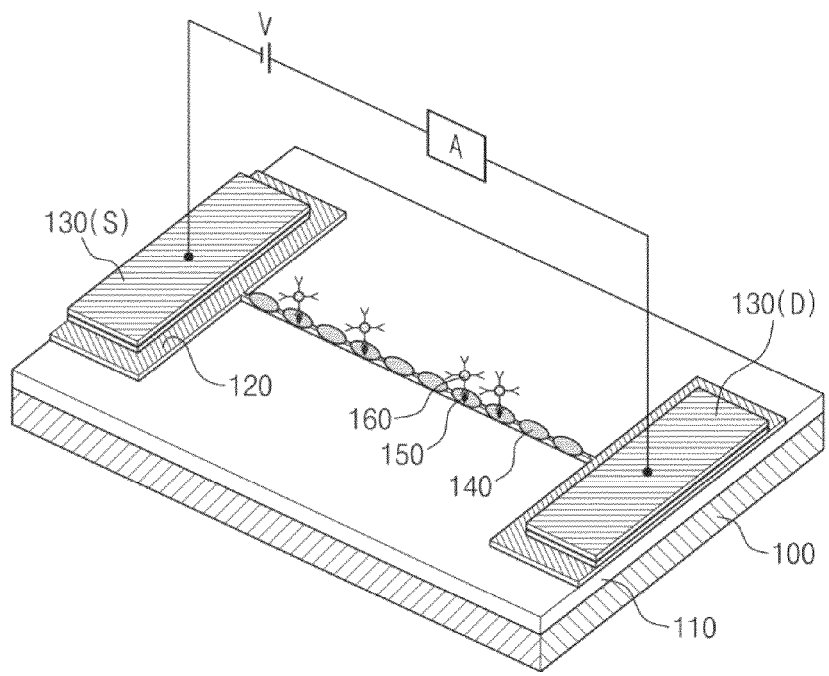

The nano-particle conjugates 160 may be a material that is specifically bonded (i.e., selectively bonded) to the target molecules 150. In this case, as shown in FIG. 5, the nano-particle conjugates 160 may be formed on the surface of the channel region CH through the target molecules 150 bonded to the receptor molecules 140. As a result, as a concentration of the target molecules 150 is higher, the nano-particle conjugates 160 are formed more. Meanwhile, according to some embodiments, the forming of the nano-particle conjugates 160 may be performed under a wet environment. According to some embodiments, the nano-particle conjugates 160 may include bio-molecules and nano-particles.

According to other embodiments, the nano-particle conjugates 160 and the target molecules 150 may be in a relationship of competitive reaction. In this case, as will be described with reference to FIGS. 17 through 19, as a concentration of the target molecule 150 is higher, the nano-particle conjugates 160 formed on the surface of the channel region CH may be reduce more.

Referring to FIG. 1 again, after a predetermined potential difference V between the source and drain electrodes S and D is formed, a current A (hereinafter, a first current $I_1$) flowing through the channel region CH is measured in operation S3. According to some embodiments, in a case of a dry measurement, after the nano-particle conjugates 160 are formed, an additional dry operation may be further performed. Additionally, in a case of a wet measurement, after the nano-particle conjugates 160 are formed, a predetermined pH adjustment operation may be further performed.

Figure 6:
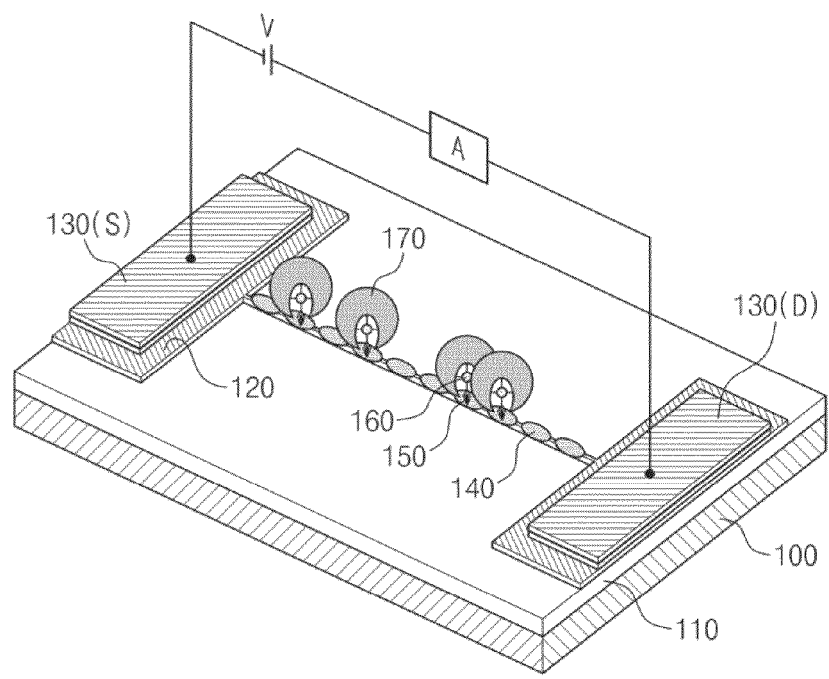

Next, as shown in FIG. 6, a process for growing a probe material 170 on the channel region CH is performed in operation S4. According to some embodiments, the probe material 170 may be a charged material that is selectively bonded to the nano-particle conjugates 160. Moreover, according to some embodiments, the process for growing the probe material 170 may be performed under a wet environment.

Due to this selective bond between the probe material 170 and the nano-particle conjugates 160, an amount of the probe material 170 is dependable on an amount of the nano-particle conjugates 160 previously formed on the channel region CH. That is, if there are a lot of the nano-particle conjugates 160, a lot of the probe materials 170 may be formed in the channel region CH. As mentioned above, as a concentration of the target molecule 150 is higher, the nano-particle conjugates 160 may be formed more. Accordingly, the probe material 170 is formed more as a concentration of the target molecule 150 is higher.

After growing the probe material 170 and generating a predetermined potential difference V between the source and drain electrodes S and D, a current A (hereinafter, a second current $I_2$) flowing through the channel region CH is measured in operation S5. According to some embodiments, the second current $I_2$ may be measured under a dry environment. For this, after the growing of the probe material 170, an additional dry operation may be further performed. However, according to modified embodiments, the second current $I_2$ may be measured under a wet environment.

According to the microanalysis method described with reference to FIGS. 1 through 6, whether there is the target molecule 150 may be confirmed from a difference $\Delta I$ between the first current $I_1$ and the second current $I_2$. For example, whether there is the target molecule 150 may be confirmed through a method of comparing the measurement current difference ($\Delta I$ or $I_2 - I_1$) with a predetermined threshold current $\Delta I_c$. That is, if the measurement current difference $\Delta I$ is greater than the threshold voltage $\Delta I_c$, it is determined that the target molecule 150 is included in the sample material.

Furthermore, whether there are the target molecules 150 may be quantitatively expressed from the current difference $\Delta I$. For example, the quantification of the target molecules 150 may be obtained on the basis of empirical data (e.g., a table or a graph) regarding a correlation between the measurement current difference $\Delta I$ and a concentration of the target molecule 150.

Figure 8:
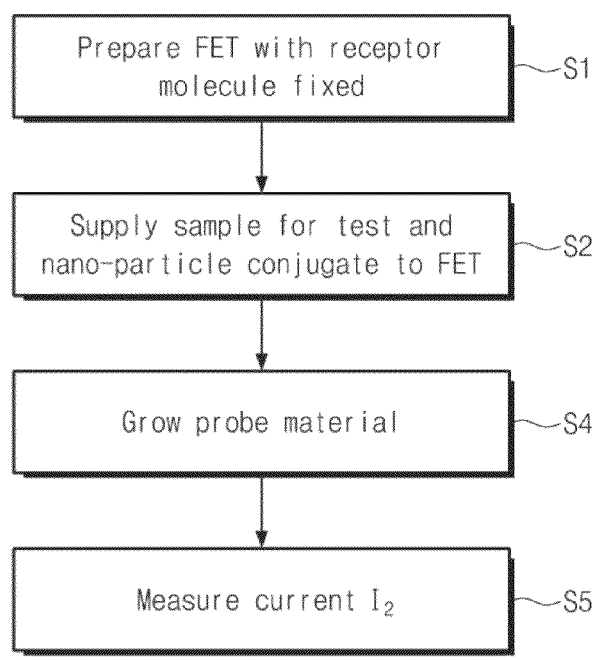
FIG. 8 is a flowchart illustrating a microanalysis method according to other embodiments of the present invention.

Moreover, according to other embodiments of the present invention, a microanalysis method may be performed without measuring the first current $I_1$, as shown in FIG. 8. That is, according to this method, the presence confirmation of the target molecule 150 or the quantification thereof may be obtained through the measurement of the second current $I_2$, which is performed after growing the probe material 170.

Figure 9:
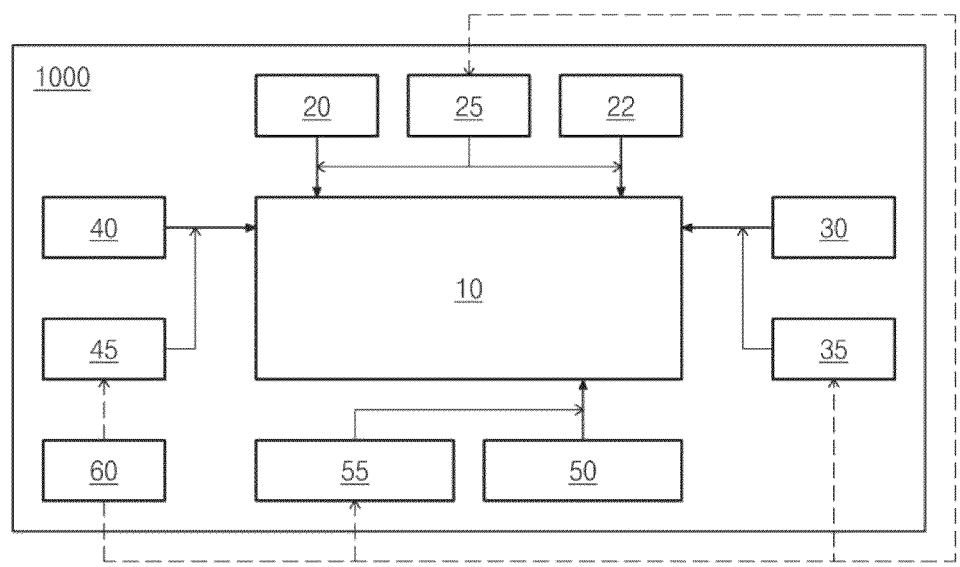
FIGS. 9 and 10 are block diagrams illustrating microanalysis systems according to embodiments of the present invention.
Figure 10:
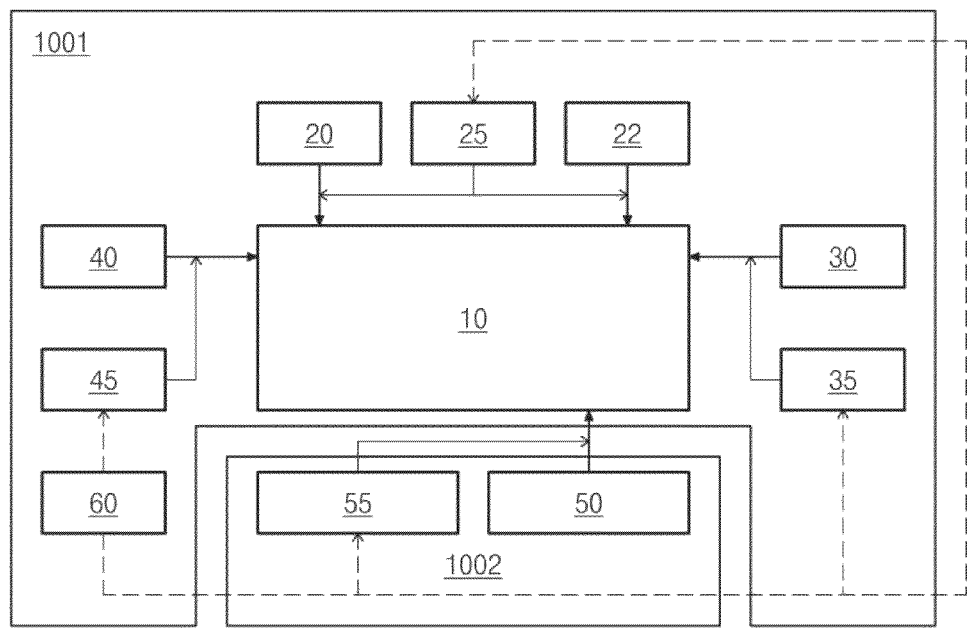

FIGS. 9 and 10 are block diagrams illustrating microanalysis systems according to embodiments of the present invention. For concise description, overlapping descriptions will be omitted.

Referring to FIGS. 9 and 10, the microanalysis systems include a FET 10, a sample supplying unit 20, a reaction material supplying unit 22, a probe material supplying unit 30, and a measuring unit 40.

The FET 10 may be those described with reference to FIGS. 2 through 7 and may include the channel region CH having the receptor molecules 140 fixed, as described with reference to FIG. 2.

The sample supplying unit 20 may be configured to supply sample materials including the target molecules 150. The receptor molecules 140 may be a material that is specifically bonded to the target molecules 150 as mentioned above.

The reaction material supplying unit 22 may be configured to supply a solution including the nano-particle conjugates 160. The nano-particle conjugates 160 may be a charged material that is specifically bonded to the target molecules 150.

The probe material supplying unit 30 may be configured to supply the probe material 170. The probe material 170 may be a charged material that is specifically bonded to the nano-particle conjugate 160.

The measuring unit 40 may include a voltage applying device configured to generate a potential difference between the source and drain electrodes S and D of the FET 10 and a current measuring device configured to measure a current flowing through the channel region CH of the FET 10. According to other embodiments, the measuring unit 40 may include a device configured to measure a gate voltage of the FET 10.

According to some embodiments of the present invention, the microanalysis system may further include a first supply controlling device 25 for controlling operations of the sample supplying unit 20 and the reaction material supplying unit 22. That is, the first supply controlling device 25 may be configured to control a process for supplying a solution including the sample materials and the nano-particle conjugates 160 from the sample supplying unit 20 and the reaction material supplying unit 22 to the channel region CH of the FET 10.

Furthermore, the microanalysis system may further include a second supply controlling device 35 configured to control a process for supplying the probe material 170 from the probe material supplying unit 30 to the channel region CH of the FET 10. Additionally, the microanalysis system may further include a measurement controlling unit 45 configured to control a process for controlling the voltage applying and current measuring processes through the measurement unit 40.

According to other embodiments, the microanalysis system may further include a reaction environment adjusting unit 50 and a reaction environment controlling unit 55 for controlling an operation thereof. The reaction environment adjusting unit 50 may be configured to control a reaction environment for a specific bonding process between the target molecules 150 and the nano-particle conjugates 160. For example, the reaction environment adjusting unit 50 may be configured to control a temperature and/or a pressure around the FET 10. However, this reaction environment may vary according to the kinds of the receptor molecules 140, the target molecules 150, and the nano-particle conjugates 160. Accordingly, the technical scopes of the present invention are limitedly not applied to a case where the reaction environment is a temperature and a pressure shown.

According to further other embodiments, the microanalysis system may further include a main controlling unit 60 configured to control operations of the first supply controlling device 25, the second supply controlling device 35, the measurement controlling unit 45, and the reaction environment controlling unit 55. The main controlling unit 60 may be further connected to a means for exchanging information with a user or an external electronic device.

Moreover, according to some embodiments of the present invention, the FET 10, the sample supplying unit 20, the reaction material supplying unit 22, the probe material supplying unit 30, the measuring unit 40, the first supply controlling device 25, the second supply controlling device 35, the measurement controlling unit 45, the reaction environment adjusting unit 50, the reaction environment controlling unit 55, and the main controlling unit 60 may be provided as one module 1000 as shown in FIG. 9.

However, according to other embodiments, they may be provided as a plurality of modules. For example, as shown in FIG. 10, the microanalysis system may include a first module 1001 including the FET 10 and a second module 1002 including the reaction environment adjusting unit 50 and the reaction environment controlling unit 55. The number of modules included in the microanalysis system or what components are included in each module may vary. Since this modification is easily realized by those skilled in that art, its descriptions will be omitted.

According to other embodiments of the present invention, the microanalysis system may not include the above-mentioned several components. For example, the microanalysis system may be realized without the reaction environment adjusting unit 50 and the reaction environment controlling unit 55 according to the kinds of the receptor molecules 140, the target molecules 150, and the nano-particle conjugates 160.

Figure 11:
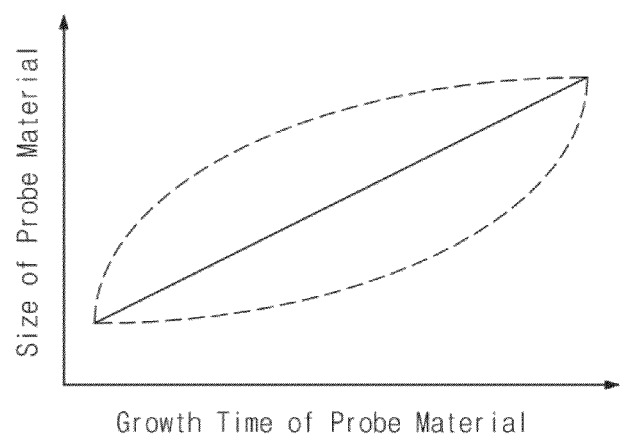
FIG. 11 is a graph illustrating one aspect of the embodiments according to the technical scopes of the present invention.

FIG. 11 is a graph illustrating one aspect of embodiments according to the technical scope of the present invention.

According to one aspect, the growth of the probe material may be dependable on a growth time of the probe material. For example, as shown in FIG. 11, as a time (e.g., a processing time of a plating operation) for growing the probe material elapses, a size of the probe particle may be monotonically increased.

A relation between the size and growth time of the probe material may be confirmed through the experiments performed by invertors. In more detail, in relation to this experiment, the FET 10 may is realized using a SOI wafer having a buried oxide of 200 nm thickness. The FET 10 is formed with 33 channel patterns and a thickness and a width of each channel pattern is about 40 nm and 180 nm, respectively. Additionally, in this experiment, monoclonal anti-Aflatoxin-$B_1$ and monoclonal anti-Aflatoxin-$B_1$-Au Nps conjugates are used for the target molecule 150 and the nano-particle conjugate 160, respectively. The receptor molecule 140 uses Aflatoxin-B1-BSA receptor molecules. The growth of the probe material in operation S4 may be performed through a plating operation using a mixture of 10 mM $HAuCl_4.3H_2O$ and 16 mM $NH_2OH.HCl$.

Figure 12:
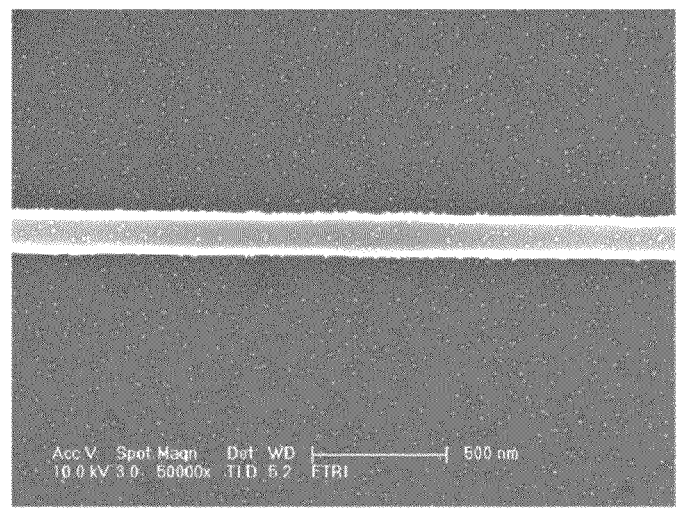
FIGS. 12 through 14 are SEM images illustrating one aspect of the embodiments according to the technical scopes of the present invention.
Figure 13:
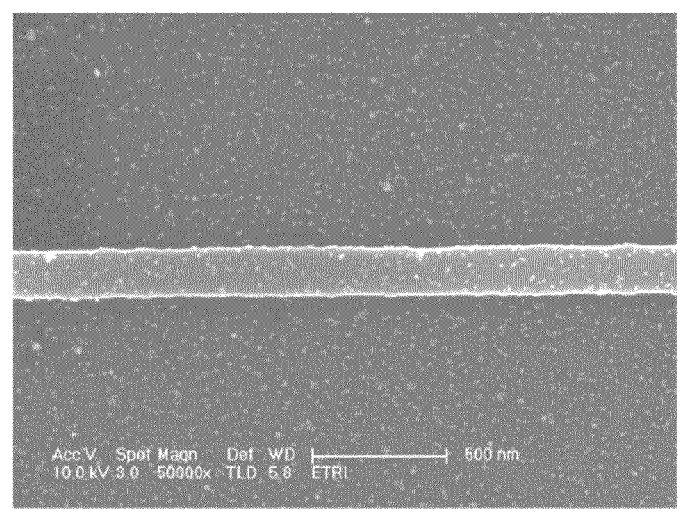
Figure 14:
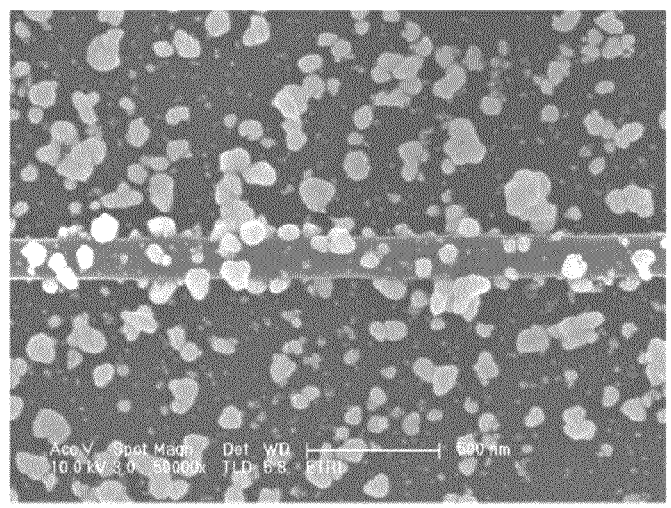

FIGS. 12 through 14 are Scanning Electron Microscope (SEM) images obtained from the experiment. In more detail, FIG. 12 is an image obtained before the plating operation is performed and FIGS. 13 and 14 are images obtained after the plating operation is performed. FIGS. 13 and 14 are images obtained at the respective about 30 sec and 90 sec processing times during the plating operation. When comparing FIGS. 12 through 14, as described with reference to FIG. 11, a size of the probe material 170 is increased as a processing time of the plating operation elapses.

Figure 15A:
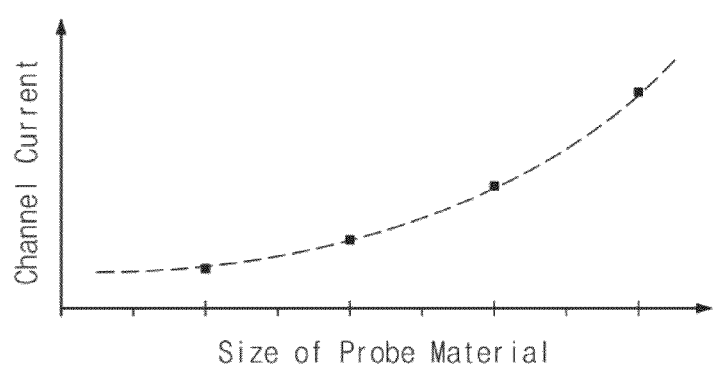
FIGS. 15A and 15B are graphs illustrating another aspect of the embodiments according to the technical scopes of the present invention.
Figure 15B:
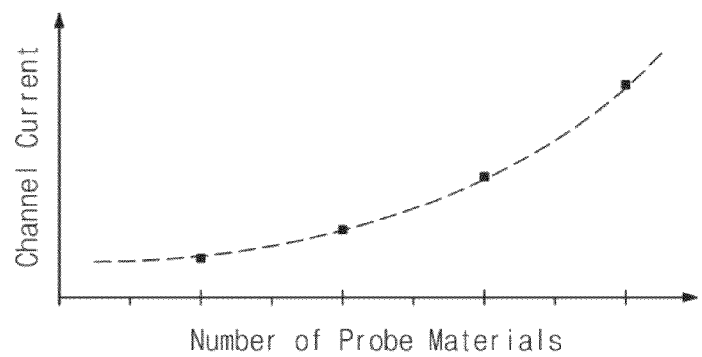
Figure 16:
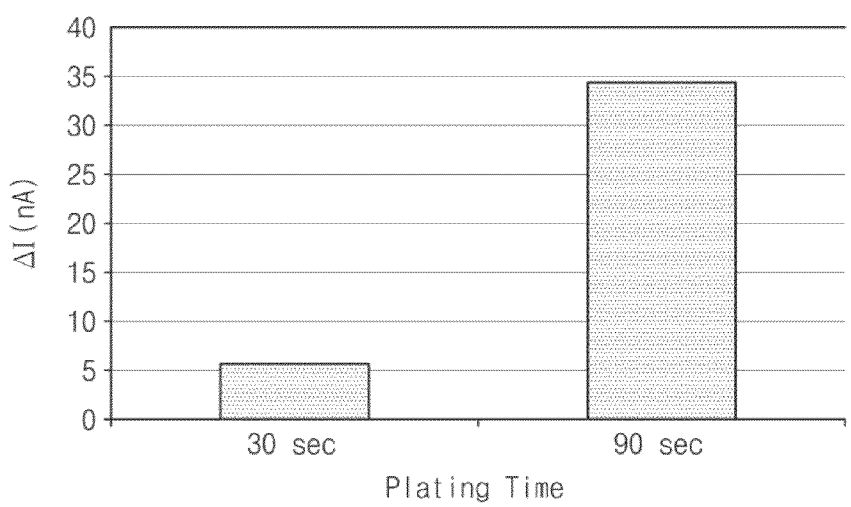
FIG. 16 is a graph illustrating an experimental result obtained by measuring a channel current difference according to a processing time of a plating operation.

FIGS. 15A and 15B are graphs illustrating another aspect of embodiments according to the technical scopes of the present invention. FIG. 16 is a graph illustrating an experimental result obtained by measuring a channel current difference according to a processing time of a plating operation.

According to another aspect, a current flowing through the channel region Ch of the FET 10 may be dependable on a size of the probe material 170. For example, as shown in FIG. 15A, as a size of the probe material 170 is increased, the channel current may be increased. As shown in FIG. 15B, as the number of probe material 170s is increased, the channel current may be increased.

A relation between the size of the probe material 170 and the channel current may be confirmed through the experiments performed by inventors. This experiment is prepared identical to that described with reference to FIG. 11 and the channel current is measured twice before and after the probe material is formed as shown in FIG. 1. The channel currents are measured under conditions of about 10 mV amplitude at about 73.83 Hz and about zero dc (and about 50 mV amplitude at about zero dc). FIG. 16 is a graph illustrating a result obtained from the measurement. In the graph, a y-axis represents a difference $\Delta I$ of the channel currents obtained by twice measurements and an x-axis represents a processing time of the plating operation. Referring to FIG. 16, the differences $\Delta I$ of the channel currents are about 5.9 nA and about 34.6 nA, respectively, when processing times of the plating operation are about 30 sec and about 90 sec, respectively. That is, the channel current difference $\Delta I$ measured at about 90 sec is about 5.86 times than that at about 30 sec. As described with reference to FIG. 11, in that a size of the probe material 170 is increased as a processing time of the plating operation is increased, the result of FIG. 16 may be interpreted as that the channel current is increased as a size of the probe material 170 is increased.

Figure 17:
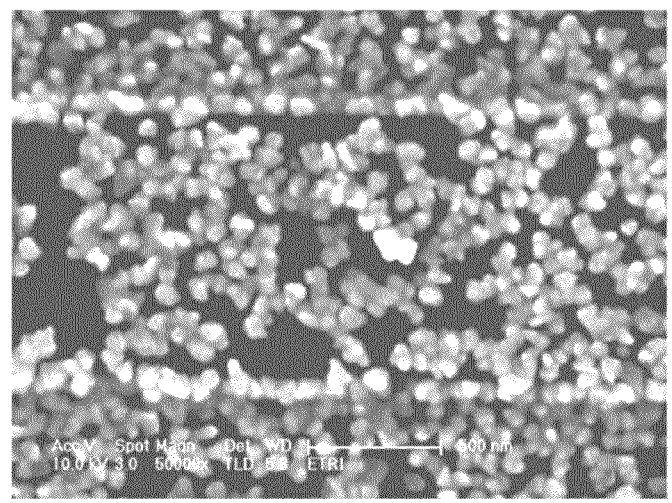
FIGS. 17 and 18 are SEM images illustrating another aspect of the embodiments according to the technical scopes of the present invention.
Figure 18:
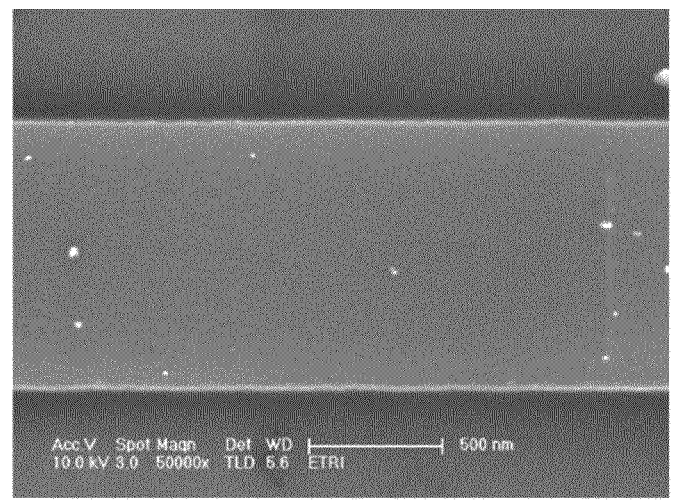

Moreover, as mentioned with reference to FIG. 5, the nano-particle conjugates 160 and the target molecules 150 may be in a relation of competitive reaction during a reaction with the receptor molecules 140. FIGS. 17 and 18 are SEM images illustrating experimental result regarding the above relation. Except a difference in a concentration of monoclonal anti-Aflatoxin-$B_1$ used as a target molecule, samples used for obtaining the images of FIGS. 17 and 18 are prepared through the same method as the experiment described with reference to FIG. 11. In more detail, FIGS. 17 and 18 are images obtained from the samples manufactured under conditions that concentrations of monoclonal anti-Aflatoxin-$B_1$ are about 1 ng/ml and about 100 ng/ml.

Referring to FIGS. 17 and 18, as a concentration of the target molecule 150 is lower, gold particles (i.e., the probe material) are generated more. In that two samples are obtained from the plating operation under the same condition, a quantitative difference of the gold particles reflects a quantitative difference of the nano-particle conjugates 160 that is specially bonded thereto. Accordingly, as mentioned above, when the nano-particle conjugate 160 and the target molecule 150 are in a relation of competitive reaction, it is confirmed that as a concentration of the target molecule 150 is higher, the nano-particle conjugates 160 are reduced.

Figure 19:
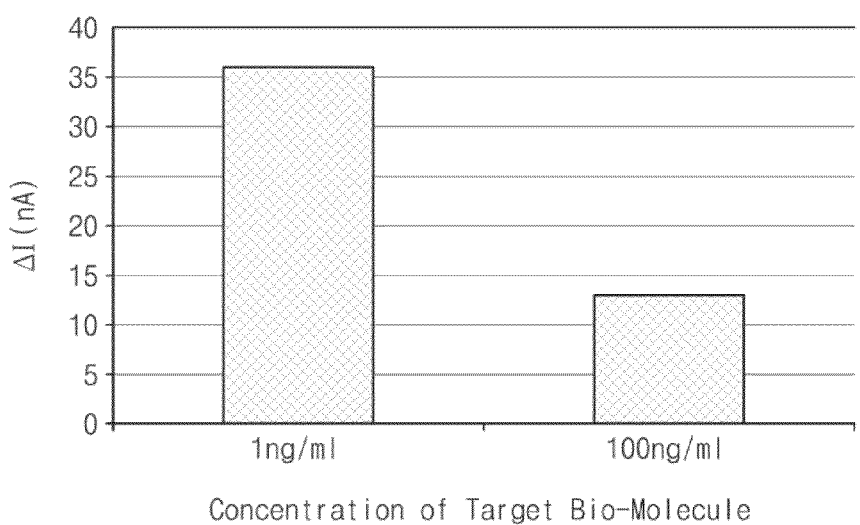
FIG. 19 is a graph illustrating an experimental result obtained by measuring a channel current according to a concentration of a target bio-molecule.

FIG. 19 is a graph illustrating an experimental result obtained by measuring a channel current difference according to a concentration of a target bio-molecule. In more detail, a y-axis of FIG. 19 represents a difference $\Delta I$ between the channel currents and an x-axis represents a concentration of the target molecule. Furthermore, FIG. 19 shows the results obtained from the samples of FIGS. 17 and 18, as shown in the x-axis.

Referring to FIG. 19, when concentrations of the target molecules 150 are about 1 ng/ml and about 100 ng/ml, differences $\Delta I$ of the channel currents are about 36 nA and about 12.7 nA, respectively. That is, as a concentration of the target molecule 150 is higher, a difference $\Delta I$ of the channel currents is reduced. This reciprocal relation may be shown as mentioned above when the nano-particle conjugate 160 and the target molecule 150 are in a relation of competitive reaction.

Moreover, FIG. 19 illustrates a case that as the number of nano-particle conjugates is greater, a channel current difference ΔI is increased, with respect to a processing time of a plating operation.

According to the embodiments of the present invention, probe materials grow from nano-particle conjugates, which are specifically bonded with target molecules to be formed in a channel region of an FET. Accordingly, an amount of the probe materials formed in the channel region has a dependency on a concentration of the target molecule.

Moreover, the probe materials may be charged materials. Accordingly, the channel current may be amplified by the grown probe materials. As a result of the current amplification, it is possible to quantitatively detect a micro material with reproducibility. Additionally, according to some embodiments of the present invention, since the probe materials grow through simple plating operations, a micro material may be detected through a simplified measurement process.

Due to the above-mentioned sequential specific bonding, the channel current has a dependency on a concentration of the target molecule but an electric potential of the channel region is dominantly determined by the probe materials not by the target molecules. When bio-molecules are detected, in order to measure influence with respect to an electric potential of the channel region due to the target molecules (i.e., bio-molecules), complex control processes (e.g., pH adjustment) is required under a wet environment. However, according to some embodiments of the present invention, the probe materials may be charged metallic materials. Accordingly, measuring of the channel current may be promptly performed under a dry environment without complex control processes.

The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A microanalysis method comprising:
   preparing a Field Effect Transistor (FET) including a channel region that has a receptor molecule, the receptor molecules being fixed on a surface of the channel region;
   supplying a sample and a solution to the FET, the sample including a target molecule and the solution including a nano-particle conjugate;
   binding the target molecule to the receptor molecule;
   binding the nano-particle conjugate to the target molecule;
   measuring a first current through the channel region after binding the target molecule to the receptor molecule and before growing a probe material;
   growing the probe material on the channel region of the FET such that the probe material binds to the nano-particle conjugate;
   measuring a second current through the channel region after growing the probe material;
   calculating a difference between the first current and the second current; and
   obtaining a concentration of the target molecule based on the calculated difference.

2. The microanalysis method of claim 1, wherein the probe material is a charged material that is selectively bonded to the nano-particle conjugate.

3. The microanalysis method of claim 1, wherein binding the target molecule to the receptor molecule includes using an immune reaction between the target molecule and the receptor molecule.

4. The microanalysis method of claim 1, wherein growing of the probe material is performed using a plating operation.

5. The microanalysis method of claim 1, wherein binding the nano-particle conjugate and growing the probe material are performed under a wet environment.

6. The microanalysis method of claim 1,
   wherein measuring the first current is performed under a wet or dry environment; and
   wherein measuring the second current is performed under a wet or dry environment.

7. The microanalysis method of claim 1, wherein the target material includes a bio-molecule; and
   wherein the nano-particle conjugate and the probe material include a metallic element.

\* \* \* \* \*